United States Patent [19]

Udovich et al.

[11] 4,328,126

[45] May 4, 1982

[54] CATALYST FOR THE PRODUCTION OF MALEIC ANHYDRIDE BY THE OXIDATION OF BUTANE

[75] Inventors: Carl A. Udovich, Joliet, Ill.; Ralph J. Bertolacini, Chesterton, Ind.

[73] Assignee: Standard Oil Company (Indiana), Chicago, Ill.

[21] Appl. No.: 139,232

[22] Filed: Apr. 11, 1980

[51] Int. Cl.$^3$ .................. B01J 23/06; B01J 23/22; B01J 27/18

[52] U.S. Cl. .................. 252/435; 252/437; 549/260

[58] Field of Search .................. 252/435, 437; 260/346.75

[56] References Cited

U.S. PATENT DOCUMENTS 3,862,146  1/1975  Boghosian .................. 260/346.75
4,151,116  4/1979  McDermott .................. 252/435

*Primary Examiner*—W. J. Shine
*Attorney, Agent, or Firm*—Gunar J. Blumberg; William T. McClain; William H. Magidson

[57] ABSTRACT

A novel catalyst for the oxidation of butane to produce maleic anhydride comprising a phosphorus and vanadium mixed oxide promoted by zinc wherein the catalyst is prepared by using an organic medium and has two specific phases identified by characteristic X-ray pattern. A process for the manufacture of maleic anhydride from butane feedstock utilizing the novel catalyst.

3 Claims, No Drawings

CATALYST FOR THE PRODUCTION OF MALEIC ANHYDRIDE BY THE OXIDATION OF BUTANE

BACKGROUND OF THE INVENTION

1. Field of the Invention

The field of this invention relates to the production of maleic anhydride from n-butane and catalysts therefor.

2. Background

Maleic anhydride is of significant commercial interest throughout the world and is extensively used in the manufacture of alkyd resins. It is also a versatile intermediate for chemical synthesis. Consequently, large quantities of maleic anhydride are produced each year to satisfy these needs. The production of maleic anhydride by the catalytic oxidation of benzene and butene is well known and the principal method currently employed for the manufacture of maleic anhydride is by the air oxidation of benzene in the presence of certain heavy metal oxide catalysts. However, because of the inherent toxicity of benzene fumes, the trend has been to eliminate the utilization of benzene as a feedstock and newer facilities tend to utilize butane oxidation processes.

In general, catalysts proposed for the oxidation of butane to maleic anhydride have been based upon vanadium and phosphorus. In U.S. Pat. No. 3,293,268 it is disclosed that the oxidation of butane to maleic anhydride can be performed in the presence of a phosphorus-vanadium-oxygen containing complex catalyst. Though this catalyst is capable of oxidizing butane, it does not give sufficiently high yields. Yields of maleic anhydride of only 30 to 50 weight percent are reported. Various activators, stabilizers and promoters have been disclosed in the prior art to improve the yields of maleic anhydride. References include U.S. Pat. Nos. 3,867,411, 3,832,359, 3,888,886, 4,002,650, 4,147,661, 4,149,992, 4,151,116, 4,152,338, 4,152,339 and British Application 2,019,839A. While the aforementioned prior art tends to bring about some improvement in the performance of the phosphorus vanadium catalyst there remains much room for improvement, particularly from the standpoint of high conversion, yield and catalyst life.

The object of the present invention is to provide a phosphorus vanadium zinc oxide catalyst prepared in an organic medium which prior to its use in the manufacture of maleic anhydride from butane feedstock is in a phase comprising in excess of eighty percent of a characteristic powder X-ray diffraction pattern using copper K alpha radiation as follows:

| d angstrom | Line Position 2.θ degrees | Intensity |
|---|---|---|
| 5.7 | 15.6 | 100 |
| 4.5 | 19.7 | 41 |
| 3.7 | 24.3 | 25 |
| 3.3 | 27.1 | 32 |
| 3.1 | 28.8 | 14 |
| 2.9 | 30.5 | 40 |
| 2.8 | 32.2 | 9 |
| 2.7 | 33.7 | 20 | which when used in the manufacture of maleic anhydride from butane at a temperature of 700° to 850° F. converts to a second base having a characteristic powder X-ray diffraction pattern using copper K alpha radiation as follows:

| d angstrom | Line Position 2.θ degrees | Intensity |
|---|---|---|
| 6.3 | 14.2 | 10 |
| 4.8 | 18.5 | 7 |
| 3.9 | 23.0 | 100 |
| 3.1 | 28.5 | 58 |
| 3.0 | 30.0 | 29 |
| 2.7 | 33.8 | 7 |

A further object is to provide a process for the manufacture of maleic anhydride from butane at a temperature of about 650° to 850° F. in the presence of the novel catalyst.

The novel catalyst comprises a phosphorus vanadium mixed oxide promoted by zinc. The atomic ratio of the vanadium to phosphorus can suitably be in the range of 0.5:1.0 to 1.25:1.0, preferably in the range of 0.6:1.0 to 1.0:1.0. The total atomic ratio of zinc to vanadium advantageously is in the range of 0.005:1 to 0.4:1. It is preferred that the total atomic ratio of zinc to vanadium should be in the range of 0.01:1 to 0.25:1. The atomic ratio of phosphorus to vanadium is suitably in the range of 0.8:1 to 2:1, preferably 1:1 to 1.7:1.

Catalysts prepared according to the invention may be made from an organic solvent system wherein vanadium pentoxide in the presence of zinc is reduced with gaseous hydrogen chloride. Subsequent reaction of the vanadium zinc oxide solution with crystalline orthophosphoric acid and removal of water of reaction by azeotropic distillation results in precipitation of a crystalline vanadium phosphorus zinc mixed oxide which may suitably be filtered from the mother liquor, dried and then employed as an oxidation catalyst for the manufacture of maleic anhydride from butane feedstock. Suitably, organic solvents are alcohols or mixtures of alcohols with aromatic hydrocarbons such as benzene and orthoxylene. Aliphatic alcohols are usually employed in the process and isobutanol is the preferred alcohol. The precipitation of the phosphorus vanadium zinc oxide complex is achieved by reducing the solubility of this complex in solution by employing a co-solvent. Precipitation can also be effected by reducing the temperature and removal of the solvent. The use of a co-solvent such as benzene or orthoxylene also functions to facilitate removal of excess water through azeotropic distillation. Precipitation of the phosphorus vanadium zinc mixed oxide can suitably be effected by azeotropic distillation of the organic solvent and the water of reaction and subsequent evaporation of the organic solvent. The zinc may be added as a compound together with vanadium or separately introduced into the solution. Suitable zinc compounds comprise metallic zinc, zinc chloride, zinc oxide and most soluble zinc salts. If it is desired to improve physical properties of the catalysts it may be treated with the suspension of an inert support for example alumina, titania, silicon carbide, kieselguhr, pumice or preferably silicon. The catalyst may be reinforced with such materials at any stage in its preparation.

According to our process, the average valence of vanadium is in the range of about 4.0 to 4.4. In our catalyst preparation, various anhydrous phosphoric acids may be used including ortho-phosphoric, pyrophosphoric, triphosphoric acid or meta-phosphoric acid. The vanadium compound can be vanadium pentoxide, vanadium tetrachloride, vanadium trichloride, vanadium oxydichloride, vanadium oxytrichloride, vanadium tetroxide, vanadium oxalate, and most soluble vanadium complexes. Suitable vanadium compounds include: vanadium oxides such as vanadium pentoxide, vanadium trioxide and the like; vanadium oxyhalides such as vanadyl chloride, vanadyl dichloride, vanadyl trichloride, vanadyl bromide, vanadyl dibromide, vanadyl tribromide and the like; vanadium containing acids such as metavanadic acid, pyrovanadic acid and the like; vanadium salts such as ammonium metavanadate, vanadium sulfate, vanadium phosphate, vanadyl formate, vanadyl oxalate and the like. However, vanadium pentoxide is preferred.

It has been discovered that the catalyst having a characteristic phase one showing an X-ray diffraction pattern as follows:

| d angstrom | Line Position 2.θ degrees | Intensity |
|---|---|---|
| 5.7 | 15.6 | 100 |
| 4.5 | 19.7 | 41 |
| 3.7 | 24.3 | 25 |
| 3.3 | 27.1 | 32 |
| 3.1 | 28.8 | 14 |
| 2.9 | 30.5 | 40 |
| 2.8 | 32.2 | 9 |
| 2.7 | 33.7 | 20 | which when utilized in the manufacture of maleic anhydride from butane feedstock at a temperature of about 650° to 850° F. has a second phase having the following X-ray pattern.

| d angstrom | Line Position 2.θ degrees | Intensity |
|---|---|---|
| 6.3 | 14.2 | 10 |
| 4.8 | 18.5 | 7 |
| 3.9 | 23.0 | 100 |
| 3.13 | 28.5 | 58 |
| 2.98 | 30.0 | 29 |
| 2.65 | 33.8 | 7 |

The aforementioned X-ray forms comprise at least eighty percent of the catalyst. This catalyst shows excellent selectivity and yield in the manufacture of maleic anhydride from butane. Also, this catalyst has a long life and can be regenerated in situ, thus, making it useful for the commercial production of maleic anhydride.

In a preferred embodiment, a solution of a vanadium compound in the hydrocarbon solvent is produced by the reduction of vanadium pentoxide with gaseous hydrogen chloride. A zinc compound, preferably metallic zinc is added to the solution prior to reduction stage. The temperature at which the vanadium oxide is reduced is in the range of 70° to 230° F., and preferably 90° to 160° F. After reduction, phosphorus is added suitably as ortho-phosphoric acid, preferably as 100 percent ortho-phosphoric acid. After precipitation of the mixed oxide and a suitable digestion period, it is filtered from the mother liquor and dried in a vacuum oven at about 200° to 250° F. under a positive nitrogen bleed. The dried mixed oxide may be activated by heating it in the presence of a hydrocarbon such as n-butane.

A catalyst for the production of maleic anhydride by the oxidation of butane which comprises a phosphorus-vanadium mixed oxide with zinc as the promoter, the atomic ratio of vanadium to phosphorus being in the range of 0.5:1 to 1.25:1 and the total atomic ratio of zinc to vanadium being in the range of 0.01:1 to 0.25:1 wherein the catalyst in the initial phase has a characteristic initial powder X-ray diffraction pattern using K alpha radiation as follows:

| d angstrom | Line Position 2.θ degrees | Intensity |
|---|---|---|
| 5.7 | 15.6 | 100 |
| 4.5 | 19.7 | 41 |
| 3.7 | 24.3 | 25 |
| 3.3 | 27.1 | 32 |
| 3.1 | 28.8 | 14 |
| 2.9 | 30.5 | 40 |
| 2.8 | 32.2 | 9 |
| 2.7 | 33.7 | 20 | which upon heating at a temperature of about 600° to 800° F. under reaction conditions for the oxidation of butane to maleic anhydride converts to a phase having a characteristic powder X-ray diffraction pattern using copper K alpha radiation as follows:

| d angstrom | Line Position 2.θ degrees | Intensity |
|---|---|---|
| 6.3 | 14.2 | 10 |
| 4.8 | 18.5 | 7 |
| 3.9 | 23.0 | 100 |
| 3.1 | 28.5 | 58 |
| 3.0 | 30.0 | 29 |
| 2.7 | 33.8 | 7 |

This invention also comprises a process for oxidizing butane to maleic anhydride by contacting it in the presence of oxygen with the novel catalyst. The oxidation of butane to maleic anhydride may be accomplished by contacting n-butane in low concentration in oxygen with the described catalyst. Air is entirely satisfactory as a source of oxygen, but synthetic manufactures of oxygen and diluent gases such as nitrogen also may be employed. Air enriched with oxygen may be used.

The gaseous feed stream to the oxidation reactors will normally contain air and about 0.2 to about 1.7 mole percent of n-butane. About 0.8 to 1.5 mole percent of n-butane is satisfactory for optimum yield of maleic anhydride for the process of this invention. Although higher concentrations may be employed, explosive hazards may be encountered. Lower concentrations of butane less than about one percent, of course, will reduce the total yield obtained at equivalent flow rates and, thus, are not normally economically employed. The flow rate of the gaseous stream through the reactor may be varied within rather wide limits, but preferred range of operations is at the rate of about 100 to 4000 cc of feed per cc of catalyst per hour and more preferably about 1000 to 2400 cc feed per cc of catalyst per hour. Residence times of the gas stream will normally be less than about four seconds, more preferably less than about one second, and down to a rate where less efficient operations are obtained. The flow rates and residence times are calculated at standard conditions of 760 mm of mercury and at 25° C. A variety of reactors will be found to be useful and multiple tube heat exchanger type reactors are quite satisfactory. The tops of such reactors may vary in diameter from about one-quarter inch to about three inches, and the length may be varied from about three to about ten or more feet. The oxidation reaction is an exothermic reaction and, therefore, relatively close control of the reaction temperatures should be maintained. It is desirable to have the surface of the reactors at a relatively constant temperature and some medium to conduct heat from the reactors is necessary to aid temperature control. Such media may be Woods metal, molten sulphur, mercury, molten lead and the like, but it has been found that eutectic salt baths are completely satisfactory. One such salt bath is a sodium nitrate, sodium nitrite-potassium nitrate eutectic constant temperature mixture. An additional method of temperature control is to use a metal block reactor whereby the metals surrounding the tube acts as a temperature regulating body. As will be recognized by a man skilled in the art, the heat exchanger medium may be kept at the proper temperature by heat exchangers and the like. The reactor or reaction tubes may be iron, stainless steel, carbon steel, nickel, glass tubes such as vycor and the like. Both carbon steel and nickel tubes have excellent long life under the conditions of the reaction described herein. Normally, the reactors contain a present heat zone under an inert material such as one-quarter inch Alundum pellets, inert ceramic balls, nickel balls, or chips and the like present at about one-half to one-tenth the volume of the active catalyst present.

The temperature of reaction may be varied within some limits but, normally the reaction should be conducted at a temperature within a rather critical range. The oxidation reaction is exothermic and once reaction is underway, the main purpose of the salt bath or other media is to conduct heat away from the balls of the reactor and control the reaction. Better operations are normally obtained when the reaction temperature employed is no greater than 20°-50° F. above the salt bath temperature. The temperature of the reactor, of course, will also depend on some extent upon the size of the reactor and the butane concentration.

The reaction may be conducted at atmospheric, superatmospheric, or below atmospheric pressure. The exit pressure will be at least slightly higher than the ambient pressure to insure a positive flow from the reaction. The pressure of the inert gases must be sufficiently higher to overcome the pressure drop through the reactor.

Maleic anhydride may be recovered by a number of ways well known to those skilled in the art. For example, the recovery may be by direct condensation or by absorption in suitable media, with specific operation and purification of the maleic anhydride. The following examples will serve to provide a fuller understanding of the invention, but it is to be understood that these examples are given for illustrative purposes only and will not be interpreted as limiting the invention in any way. In the examples the terms "conversion", "selectivity" and "yield" are defined as follows:

$$\text{Conversion \%} = \frac{\text{Moles hydrocarbon reacted}}{\text{Moles hydrocarbon in feed}} \times 100$$

$$\text{Selectivity \%} = \frac{\text{Moles maleic produced}}{\text{Moles hydrocarbon feed consumed}} \times 100$$

$$\text{Yield Wt. \%} = (\text{Conversion}) \times (\text{Selectivity}) \times 1.69$$

EXAMPLE 1

To a 2-1 4-neck flask equipped with mechanical stirrer, reflux condenser, thermometer, barrett trap, submersible gas inlet tube and capable of being heated by an electric mantle are charged 750 ml of methanol, 91 g (0.5 gfw) vanadium pentoxide, and 6.5 g (0.1 gaw) 20 mesh zinc. Gaseous hydrogen chloride is introduced at such a rate as not to be detected at the condenser outlet. The solution warms to reflux. The reaction proceeds smoothly and the solution becomes homogeneous red-brown without any suspended solids. To assure reaction, HCl is added for an additional 30 minutes. After reaction, 125 g (1.28 gfw) of crystalline ortho-phosphoric acid is added in 100 ml of additional methanol and the mixture brought to reflux. Benzene (250 ml) is added and the solution is refluxed overnight. Solvent is removed and solids precipitate. The solids (blue) are filtered, washed with methanol and dried in a vacuum oven at 20 lbs. with an $N_2$ bleed at 225° F.

A sample of this mixed oxide was analyzed by X-ray and gave the following results:

| | Line Position | |
|---|---|---|
| d angstrom | 2.θ degrees | Intensity |
| 5.7 | 15.6 | 100 |
| 4.5 | 19.7 | 41 |
| 3.7 | 24.3 | 25 |
| 3.3 | 27.1 | 32 |
| 3.1 | 28.8 | 14 |
| 2.9 | 30.5 | 40 |
| 2.8 | 32.2 | 9 |
| 2.7 | 33.7 | 20 |

EXAMPLE 2

The same experimental setup and conditions as in example (1), but using 91 g (0.5 gfw) vanadium pentoxide, 19.6 g (0.3 gaw) 20 mesh zinc and 750 ml methanol are used to produce mixed oxide (2).

EXAMPLE 3

The mixed oxides prepared in examples (1) and (2) are combined with 5 percent sterotex and formed into ⅛" pills for catalyst evaluation. A 4 g loading of the mixed oxides is placed in a mini reactor under a 1.05 percent butane-synthetic air mixture and heated to 250°-300° F. for two hours to remove sterotex. The mixed oxides were then raised to desired reaction temperatures over the next four hours and analysis for maleic anhydride is done by gas liquid partition chromatography. The results are shown in Tables I and II.

A sample of the catalyst was submitted for X-ray analysis and gave the following results:

| | Line Position | |
|---|---|---|
| d angstrom | 2.θ degrees | Intensity |
| 6.3 | 14.2 | 10 |
| 4.8 | 18.5 | 7 |
| 3.9 | 23.0 | 100 |
| 3.1 | 28.5 | 58 |
| 3.0 | 30.0 | 29 |
| 2.7 | 33.8 | 7 |

TABLE I

MIXED OXIDE PREPARED AS IN EXAMPLE 1 AND HAVING X-RAY DIFFRACTION PATTERN SHOWN IN EXAMPLE 3

| Time on Stream (hrs) | Conversion (butane) | Selectivity (maleic) | Yield (maleic) | Temp. (°F.) |
|---|---|---|---|---|
| 24 | 86 | 53 | 77 | 802 |
| 168 | 84 | 60.5 | 86 | 802 |

TABLE I-continued

MIXED OXIDE PREPARED AS IN EXAMPLE 1
AND HAVING X-RAY DIFFRACTION PATTERN
SHOWN IN EXAMPLE 3

| Time on Stream (hrs) | Conversion (butane) | Selectivity (maleic) | Yield (maleic) | Temp. (°F.) |
| --- | --- | --- | --- | --- |
| 700 | 81 | 60.6 | 83 | 803 |

TABLE II

MIXED OXIDE PREPARED AS SHOWN
IN EXAMPLE 2 AND HAVING X-RAY
DIFFRACTION PATTERN SHOWN IN EXAMPLE 3

| Time on Stream (hrs) | Conversion (butane) | Selectivity (maleic) | Yield (maleic) | Temp. (°F.) |
| --- | --- | --- | --- | --- |
| 48 | 85 | 50 | 71 | 736 |
| 168 | 84 | 57 | 81 | 759 |
| 336 | 80 | 60 | 81 | 772 |

We claim:

1. A catalyst for the production of maleic anhydride by the oxidation of butane which consists essentially of a phosphorus-vanadium mixed oxide with zinc as the promoter, wherein vanadium pentoxide in the presence of zinc is reduced and subsequently the vanadium zinc oxide solution is reacted with phosphoric acid, the atomic ratio of vanadium to phosphorus being in the range of 0.5:1 to 1.25:1 and the total atomic ratio of zinc to vanadium being in the range of 0.01:1 to 0.25:1 wherein the catalyst in the initial phase has a characteristic initial powder X-ray diffraction pattern using copper K alpha radiation as follows:

| d angstrom | Line Position 2.θ degrees | Intensity |
| --- | --- | --- |
| 5.7 | 15.6 | 100 |
| 4.5 | 19.7 | 41 |
| 3.7 | 24.3 | 25 |
| 3.3 | 27.1 | 32 |
| 3.1 | 28.8 | 14 |
| 2.9 | 30.5 | 40 |
| 2.8 | 32.2 | 9 |
| 2.7 | 33.7 | 20 | which upon heating at a temperature of about 600° to 800° F. under reaction conditions for the oxidation of butane to maleic anhydride converts to a phase having a characteristic powder X-ray diffraction pattern using copper K alpha radiation as follows:

| d angstrom | Line Position 2.θ degrees | Intensity |
| --- | --- | --- |
| 6.3 | 14.2 | 10 |
| 4.8 | 18.5 | 7 |
| 3.9 | 23.0 | 100 |
| 3.1 | 28.5 | 58 |
| 3.0 | 30.0 | 29 |
| 2.7 | 33.8 | 7 |

2. The catalyst of claim 1, wherein there are 0.8:1 to 2:1 atoms of phosphorus present for each atom of vanadium.

3. The catalyst of claim 1, wherein from 0.01 to 0.25 atoms of zinc are present for each atom of vanadium.

* * * * *